(12) United States Patent
Nishide et al.

(10) Patent No.: US 7,949,088 B2
(45) Date of Patent: May 24, 2011

(54) X-RAY CT APPARATUS AND METHOD FOR PROCESSING X-RAY PROJECTION DATA

(75) Inventors: Akihiko Nishide, Tokyo (JP); Makoto Gohno, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 468 days.

(21) Appl. No.: 12/252,095

(22) Filed: Oct. 15, 2008

(65) Prior Publication Data

US 2009/0097611 A1    Apr. 16, 2009

(30) Foreign Application Priority Data

Oct. 15, 2007    (JP) .................................. 2007-267679

(51) Int. Cl.
*A61B 6/03*    (2006.01)
(52) U.S. Cl. .................................. 378/5; 378/4; 378/16
(58) Field of Classification Search .................. 378/4, 5, 378/16
See application file for complete search history.

(56) References Cited

U.S. PATENT DOCUMENTS

| | | | |
|---|---|---|---|
| 4,355,331 A | 10/1982 | Georges et al. |
| 4,499,493 A | 2/1985 | Nishimura |
| 4,792,900 A | 12/1988 | Sones et al. |
| 5,301,107 A | 4/1994 | Shimura |
| 5,402,338 A | 3/1995 | Ito |
| 5,782,762 A | 7/1998 | Vining |
| 5,812,691 A | 9/1998 | Udupa et al. |
| 5,813,984 A | 9/1998 | Haaga et al. |
| 5,838,758 A | 11/1998 | Krug et al. |
| 5,953,444 A | 9/1999 | Joseph et al. |
| 6,069,634 A | 5/2000 | Gibson |
| 6,106,464 A | 8/2000 | Bass et al. |
| 6,169,817 B1 | 1/2001 | Parker et al. |
| 6,173,034 B1 | 1/2001 | Chao |
| 6,205,348 B1 | 3/2001 | Giger et al. |
| 6,343,111 B1 | 1/2002 | Avinash et al. |
| 6,556,196 B1 | 4/2003 | Blanz et al. |
| 6,597,759 B2 | 7/2003 | Mazess et al. |
| 6,917,697 B2 | 7/2005 | Avinash et al. |
| 7,397,886 B2 | 7/2008 | Avinash et al. |
| 2003/0197704 A1 | 10/2003 | Tek et al. |
| 2004/0028181 A1 | 2/2004 | Charles, Jr. et al. |
| 2008/0095303 A1* | 4/2008 | Grass et al. ................. 378/5 |

FOREIGN PATENT DOCUMENTS

| | | |
|---|---|---|
| JP | 2003-037778 | 2/2003 |
| JP | 2008154669 A  * | 7/2008 |

\* cited by examiner

*Primary Examiner* — Edward J Glick
*Assistant Examiner* — John M Corbett
(74) *Attorney, Agent, or Firm* — Armstrong Teasdale LLP

(57) ABSTRACT

An X-ray CT apparatus includes an X-ray irradiation unit for applying X-rays based on a first X-ray tube voltage and X-rays based on a second X-ray tube voltage to a subject by being switched every one view, a projection data acquisition unit for acquiring projection data by which X-ray tube voltage information about the applied X-rays are identified, and an image reconstruction unit for identifying first energy projection data based on the first X-ray tube voltage, second energy projection data based on the second X-ray tube voltage, and transient energy projection data acquired upon switching between the first and second X-ray tube voltages based on the X-ray tube voltage information, the image reconstruction unit including a conversion processor that converts the transient energy projection data to another data using the transient energy projection data and performs image reconstruction using the data subsequent to the conversion process.

20 Claims, 12 Drawing Sheets

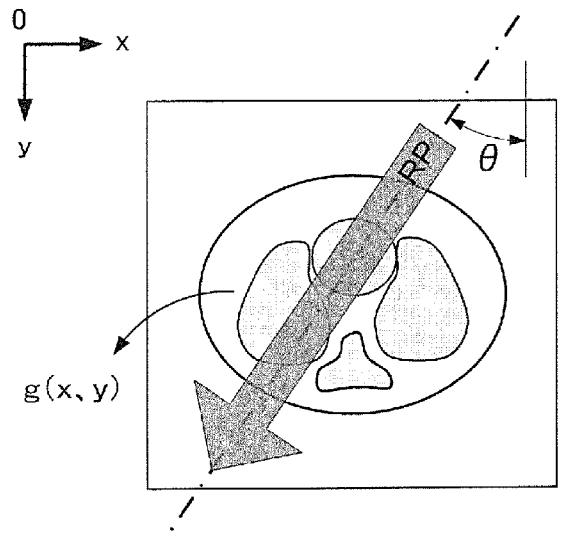
FIG. 7
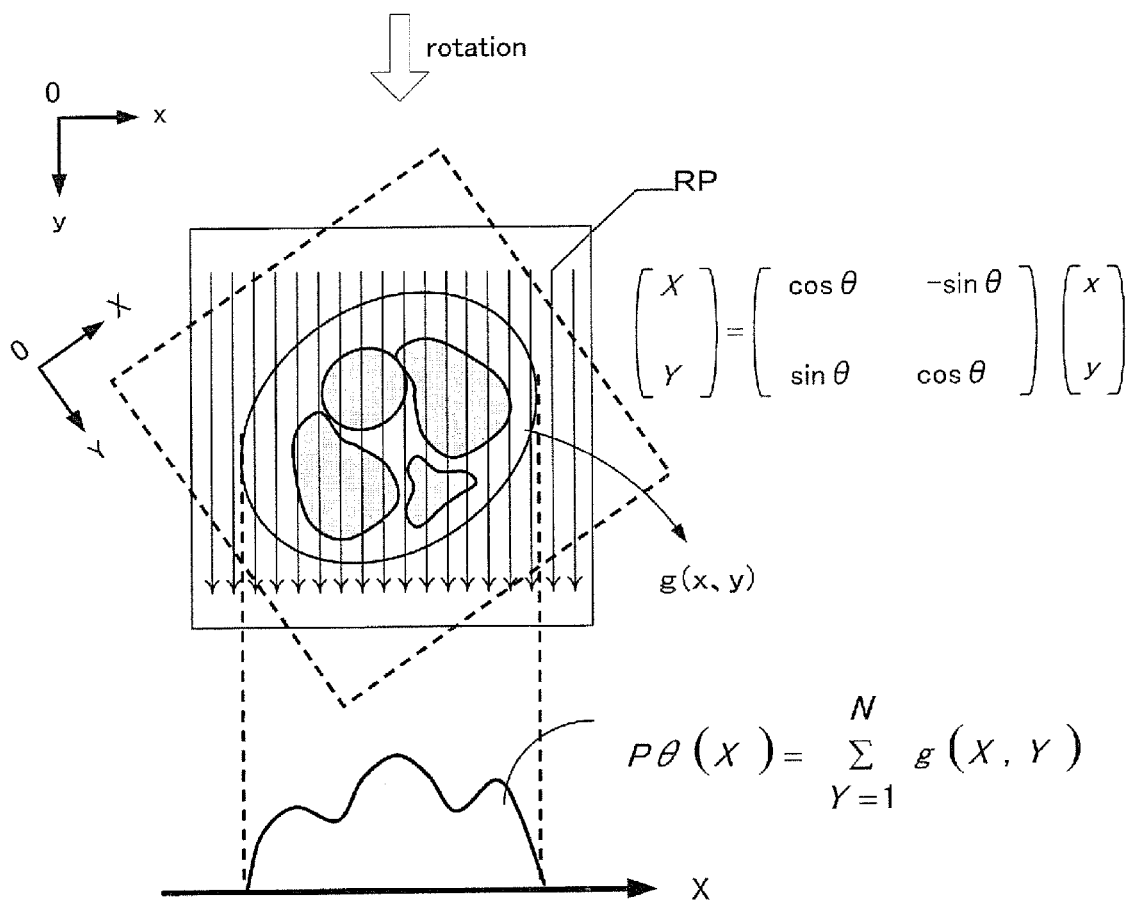

g(x, y)

X-RAY CT APPARATUS AND METHOD FOR PROCESSING X-RAY PROJECTION DATA

CROSS REFERENCE TO RELATED APPLICATIONS

This application claims the benefit of Japanese Patent Application No. 2007-267679 filed Oct. 15, 2008, which is hereby incorporated by reference in its entirety.

BACKGROUND OF THE INVENTION

The subject matter disclosed herein relates to a dual energy scan technique suitable for use in an X-ray CT apparatus.

A technique for a dual energy scan at an X-ray CT apparatus comprising one X-ray tube and one multi-row X-ray detector has been disclosed in, for example, Japanese Unexamined Patent Publication No. 2003-37778. In the dual energy scan at such a conventional X-ray CT apparatus, imaging or scanning was first conducted at a low X-ray tube voltage and the X-ray tube voltage was then raised to perform scanning at the high X-ray tube voltage. According to the present method, a time difference for raising the X-ray tube voltage has occurred between the scans. It is therefore considered that a miss registration artifact occurs due to the body motion, heartbeat, pulsation, breathing, peristalsis or the like of a subject or subject upon this scan, and thereby image quality is degraded.

BRIEF DESCRIPTION OF THE INVENTION

Therefore, an X-ray CT apparatus for switching X-ray tube voltages at high speed every view or plural views has been considered to reduce the miss registration artifact upon the dual energy scan at the X-ray CT apparatus comprising one X-ray tube and one multi-row X-ray detector. In the X-ray CT apparatus, however, the proportion of an X-ray tube voltage (hereinafter defined as transient tube voltage) in a transient state developed while the X-ray tube voltage is shifted from a low X-ray tube voltage to a high X-ray tube voltage, increases as the X-ray tube voltage is changed at high speed. Therefore, the number of X-ray projection data unused in image reconstruction, corresponding to the transient tube voltage increases and thereby the efficiency of utilization of X-rays is degraded, thus leading to increases in image-quality degradation and needless exposure.

Therefore, it is an object of the present invention to realize a reduction in exposure and an improvement in image quality by improving X-ray utilization efficiency upon dual energy scanning every view or plural views.

An X-ray CT apparatus according to a first aspect comprises an X-ray irradiation unit for applying X-rays based on a first X-ray tube voltage and an X-ray based on a second X-ray tube voltage different from the first X-ray tube voltage to a subject by being switched every at least one view, a projection data acquisition unit for acquiring projection data of the X-rays applied to the subject, the projection data identifying X-ray tube voltage information about the applied X-rays, and an image reconstruction unit for identifying first energy projection data of the X-ray based on the first X-ray tube voltage, second energy projection data of the X-ray based on the second X-ray tube voltage, and transient energy projection data acquired upon switching between the first X-ray tube voltage and the second X-ray tube voltage, based on the X-ray tube voltage information, the image reconstruction unit including a conversion processor for converting at least the transient energy projection data to another data using the transient energy projection data, and performing image reconstruction using at least the data subsequent to the conversion process.

An X-ray CT apparatus according to a second aspect is provided wherein in the X-ray CT apparatus according to the first aspect, the conversion processor performs an X-ray tube voltage correcting process using X-ray tube voltage correction coefficients for correcting the transient energy projection data to projection data equivalent to a predetermined X-ray tube voltage.

An X-ray CT apparatus according to a third aspect is provided wherein in the X-ray CT apparatus according to the second aspect, the X-ray tube voltage correcting process identifies a substance of the subject with respect to the transient energy projection data and uses an X-ray tube voltage correction coefficient corresponding to the substance.

An X-ray CT apparatus according to a fourth aspect is provided wherein in the X-ray CT apparatus according to the second or third aspect, the identification of the substance of the subject with respect to the transient energy projection data is performed based on projection data obtained by performing a reprojection process on a dual energy tomographic image based on weighted addition of the first energy projection data and the second energy projection data, or a dual energy tomographic image obtained by weighted adding a first tomographic image based on the first X-ray projection data and a second tomographic image based on the second X-ray projection data.

An X-ray CT apparatus according to a fifth aspect is provided wherein in the X-ray CT apparatus according to the fourth aspect, the dual energy tomographic image includes at least one of a water equivalent image, a fat equivalent image, a bone equivalent image or a contrast agent equivalent image.

An X-ray CT apparatus according to a sixth aspect is provided wherein in the X-ray CT apparatus according to the third aspect, the X-ray tube voltage correcting process includes a process for correcting the first energy projection data, the second energy projection data and the transient energy projection data to projection data equivalent to the same X-ray tube voltage.

An X-ray CT apparatus according to a seventh aspect is provided wherein in the X-ray CT apparatus according to the third aspect, the image reconstruction unit image-reconstructs a tomographic image equivalent to a desired X-ray tube voltage, based on the post-correction first energy projection data, second energy projection data and transient energy projection data.

An X-ray CT apparatus according to an eighth aspect is provided wherein in the X-ray CT apparatus according to the sixth aspect, the X-ray tube voltage correcting process includes a process for verifying whether the correction of the transient energy projection data is proper.

An X-ray CT apparatus according to a ninth aspect is provided wherein in the X-ray CT apparatus according to the first aspect, the conversion processor calculates X-ray projection data substituted for the transient energy projection data by interpolation processing based on the first energy projection data and the second energy projection data, extracts a noise variable component from the transient energy projection data and performs a noise reducing process using the noise variable component on the X-ray projection data substituted for the transient energy projection data.

An X-ray CT apparatus according to a tenth aspect is provided wherein in the X-ray CT apparatus according to the ninth aspect, the conversion processor includes a process for correcting the first energy projection data and the second energy projection data to projection data equivalent to the same X-ray tube voltage.

An X-ray CT apparatus according to an eleventh aspect is provided wherein in the X-ray CT apparatus according to the tenth aspect, the interpolation processing based on the first energy projection data and the second energy projection data is interpolation processing using the post-correction first energy projection data and second energy projection data.

An X-ray CT apparatus according to a twelfth aspect is provided wherein in the X-ray CT apparatus according to the tenth or eleventh aspect, the image reconstruction unit image-reconstructs a tomographic image equivalent to a desired X-ray tube voltage, based on the post-correction first energy projection data and second energy projection data, and the data subjected to the noise reducing process.

An X-ray CT apparatus according to a thirteenth aspect is provided wherein in the X-ray CT apparatus according to any of the first through twelfth aspects, the X-ray irradiation unit performs either a 360° full scan by two scans or a 180°+ fan angle half scan by two scans.

An X-ray CT apparatus according to a fourteenth aspect is provided wherein in the X-ray CT apparatus according to the thirteenth aspect, the X-ray irradiation unit interchanges the first X-ray tube voltage and the second X-ray tube voltage at a first scan and a second scan.

An X-ray CT apparatus according to a fifteenth aspect is provided wherein in the X-ray CT apparatus according to any of the first through twelfth aspects, the image reconstruction unit calculates first or second energy projection data in a view direction insufficient to acquire X-ray projection data based on a first X-ray tube voltage by a 360° full scan or a 180°+ fan angle by interpolation processing.

According to the X-ray CT apparatus of the present invention, an advantage is brought about in that an X-ray CT apparatus can be realized wherein a conversion process for converting the transient energy projection data to different data is conducted upon scanning or imaging for switching X-ray tube voltages every at least one view, and at least the data subsequent to the conversion process are used in image reconstruction, whereby exposure is reduced and image quality is further improved.

A method for processing X-ray projection data according to a sixteenth aspect, comprising steps of: a step for identifying first energy projection data of X-rays based on a first X-ray tube voltage, second energy projection data of X-rays based on a second X-ray tube voltage different from the first X-ray tube voltage, and transient energy projection data acquired upon switching between the first X-ray tube voltage and the second X-ray tube voltage, based on X-ray tube voltage information identified for projection data obtained by X-ray CT apparatus, wherein said projection data being acquired by irradiating X-rays based on the first X-ray tube voltage and X-rays based on the second X-ray tube voltage to a subject by being switched every at least one view; a step for conversion processing at least the transient energy projection data to another data using the transient energy projection data; and a step for performing image reconstruction using at least the data subsequent to the conversion process.

A method for processing X-ray projection data according to a seventeenth aspect is provided wherein in the method according to the sixteenth aspect, wherein said step for conversion processing performs an X-ray tube voltage correcting process using X-ray tube voltage correction coefficients for correcting the transient energy projection data to projection data equivalent to a predetermined X-ray tube voltage.

A method for processing X-ray projection data according to an eighteenth aspect is provided wherein in the method according to the seventeenth aspect, wherein said step for conversion processing includes a process for correcting the first energy projection data, the second energy projection data and the transient energy projection data to projection data equivalent to the same X-ray tube voltage.

A method for processing X-ray projection data according to a nineteenth aspect is provided wherein in the method according to the sixteenth aspect, wherein said step for conversion processing calculates X-ray projection data substituted for the transient energy projection data by interpolation processing based on the first energy projection data and the second energy projection data, extracts a noise variable component from the transient energy projection data and performs a noise reducing process using the noise variable component on the X-ray projection data substituted for the transient energy projection data.

BRIEF DESCRIPTION OF THE DRAWINGS

FIG. 7 is a diagram showing a method of rotating a tomographic image in a θ direction to perform a reprojection process RP.

DETAILED DESCRIPTION OF THE INVENTION

Figure 1:
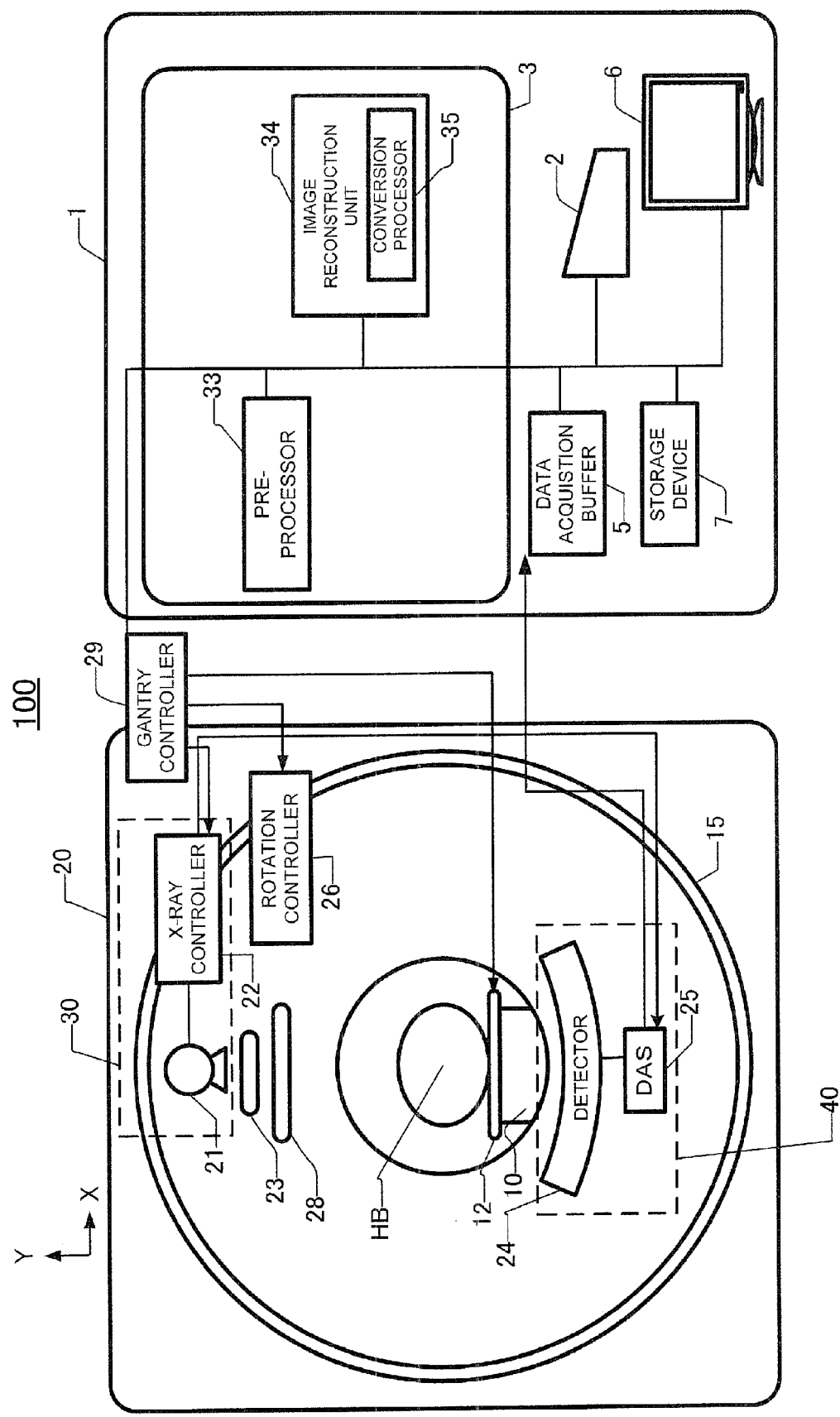
FIG. 1 is a block diagram showing an X-ray CT apparatus.

FIG. 1 is a configuration block diagram showing an X-ray CT apparatus 100 according to an embodiment of the present invention. The X-ray CT apparatus 100 is equipped with an operation console 1, an imaging or photographing table 10 and a scan gantry 20.

The operation console 1 includes an input device 2 such as a keyboard or mouse or the like, which accepts an input from an operator, a central processing unit 3 which executes a pre-process, an image reconstructing process, a post-process, etc., and a data acquisition buffer 5 which acquires or collects X-ray detector data acquired by the scan gantry 20. Further, the operation console 1 includes a monitor 6 which displays a tomographic image image-reconstructed from projection data obtained by pre-processing the X-ray detector data, and a storage device 7 which stores programs, X-ray detector data, projection data and X-ray tomographic images therein. An input for imaging or photographing conditions is inputted from the input device 2 and stored in the storage device 7. The photographing table 10 includes a cradle 12 that draws and inserts a subject or subject HB from and into a bore or aperture of the scan gantry 20 with the subject HB placed thereon. The cradle 12 is elevated and moved linearly by a motor built in the photographing table 10.

The scan gantry 20 includes an X-ray tube 21, an X-ray controller 22, a multi-row X-ray detector 24, and a data acquisition system (DAS) 25. A collimator 23, a beam forming X-ray filter 28 and an X-ray filter are disposed between the X-ray tube 21 and the subject HB. Further, the scan gantry 20 includes a rotation controller 26 which performs rotation control on a rotating section 15 having the X-ray tube 21 or the like, which is rotated about a body axis of the subject HB, and a gantry controller 29 which swaps control signals or the like with the operation console 1 and the photographing table 10. The X-ray controller 22 controls an X-ray tube voltage and an X-ray tube current mA for the X-ray tube 21. Incidentally, an X-ray irradiation unit or section 30 includes the X-ray tube 21 and the X-ray controller 22. A projection data acquisition unit or section 40 includes the multi-row X-ray detector 24 and the data acquisition system (DAS) 25. Incidentally, X-ray tube voltage information can be obtained by X-ray tube voltage reference channels installed or located in the X-ray controller 22 or the multi-row X-ray detector 24 or the like during X-ray projection data acquisition. When the X-ray tube voltage information are obtained from the X-ray controller 22, the X-ray tube voltage information are transferred from the X-ray controller 22 to the data acquisition system 25 and added to respective views of X-ray projection data. The X-ray tube voltage information for the respective views are transmitted from the X-ray controller 22 to the data acquisition system 25 as separate files and transmitted to the central processing unit 3 via the data acquisition buffer 5 by the data acquisition system 25. Thereafter, the X-ray tube voltage information can also be associated with the X-ray projection data. Incidentally, the path for the data is not limited to the above.

The beam forming X-ray filter 28 is a filter which increases X-rays directed to the center of rotation corresponding to the center of photography or imaging and decreases an X-ray dosage at its peripheral portion. Therefore, the body surface of the subject HB, which is near a circular or elliptic form, can be less exposed to radiation.

The central processing unit 3 has a pre-processor 33 and an image reconstruction unit 34.

The pre-processor 33 corrects channel-to-channel sensitivity ununiformity with respect to raw data acquired by the data acquisition system 25 and executes a pre-process such as an X-ray dosage correction for correcting an extreme reduction in signal strength or signal omission due to an X-ray strong absorber, principally, a metal portion. Further, the pre-processor 33 performs a beam hardening process.

The image reconstruction unit 34 receives projection data pre-processed at the pre-processor 33 and reconstructs an image, based on the projection data. The projection data is subjected to Fast Fourier Transform (FFT) for performing transformation into a frequency domain or region and overlaid with a reconstruction function Kernel(j), followed by being subjected to inverse Fourier transformation. The image reconstruction unit 34 performs a three-dimensional back-projection process on the projection data overlaid with the reconstruction function Kernel (j) to determine a tomographic image (xy plane) for each body-axis direction (Z-axis direction) of the subject HB. The image reconstruction unit 34 stores the tomographic image in the storage device 7.

The image reconstruction unit 34 image-reconstructs a two-dimensional distribution tomographic image of X-ray tube voltage dependent information related to a distribution of a predetermined substance (atoms), so-called tomographic image for dual energy photography or scanning from projection data RE1 at a low X-ray tube voltage kV1 and projection data RE2 at a high X-ray tube voltage kV2. As the tomographic images for the dual energy scanning, a moisture or water equivalent image, a fat equivalent image, a contrast agent equivalent image and a bone equivalent image or the like can be obtained.

The image reconstruction unit 34 includes a conversion processor 35 for converting at least transient energy projection data into different data. The transient energy projection data will be explained later in detail. The data converted by the conversion processor 35 are used in the above image reconstruction.

The dual energy scanning using the X-ray CT apparatus 100 according to the present embodiment will next be explained.

As for the dual energy scanning, there are considered a method that needs scans corresponding to two rotations and a method that may simply perform a scan corresponding to one rotation, in order to obtain one dual energy tomographic image. As the method that needs the scans corresponding to the two rotations, there are known a method using a scan corresponding to one rotation at a low X-ray tube voltage kV1 and a scan corresponding to one rotation at a high X-ray tube voltage kV2, and a method for switching between X-ray tube voltages every view or plural views. In the method that may simply perform the scan corresponding to one rotation, X-ray tube voltages are switched every view or plural views to perform imaging and insufficient views are interpolated, whereby X-ray projection data at a low X-ray tube voltage kV1 and a high X-ray tube voltage kV2 can be obtained.

Figure 2:
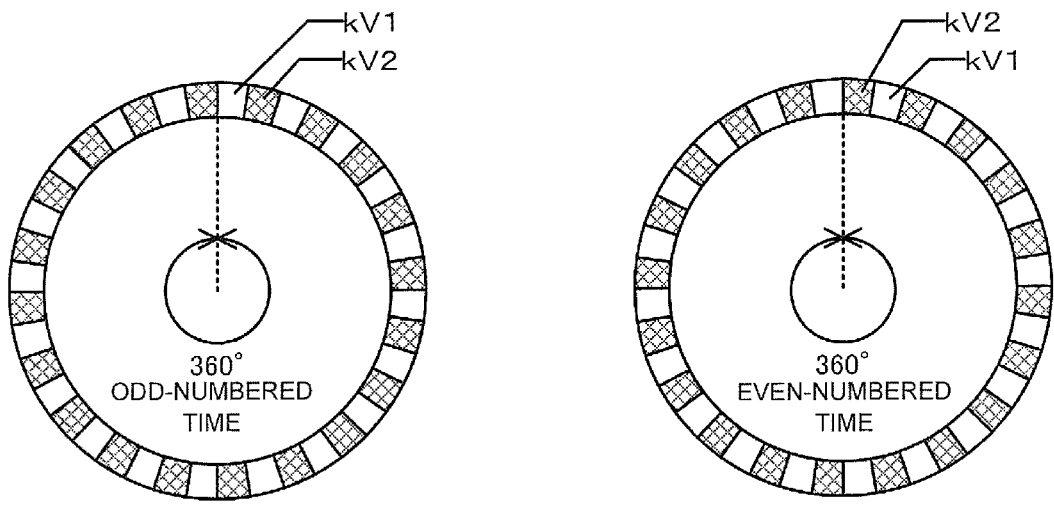
FIG. 2(*a*) is a diagram illustrating two scans corresponding to a 360° full scan at which X-ray tube voltages are switched, and FIG. 2(*b*) is a diagram depicting two scans corresponding to a 180°+ fan angle half scan at which X-ray tube voltages are switched.
Figure 2:
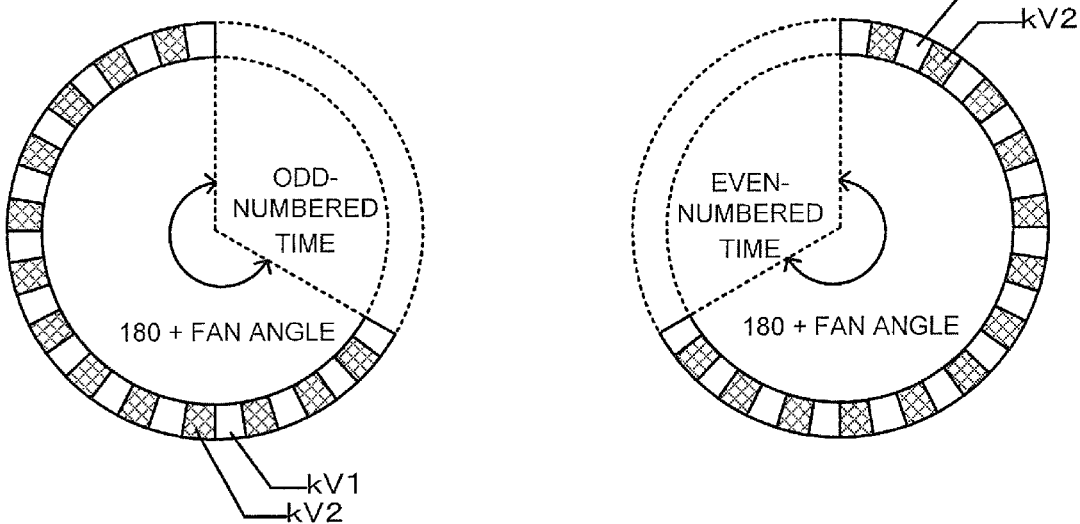

The dual energy scanning using the scans corresponding to the two rotations can be divided into such a 360° full scan F-Scan as shown in FIG. 2(*a*) and such a 180°+ fan angle half scan H-Scan as shown in FIG. 2(*b*).

In the case of the full scan F-Scan, start views for respective X-ray tube voltages are shifted at odd-numbered and even-numbered times as shown in FIG. 2(*a*), thereby making it possible to acquire X-ray projection data corresponding to 360° free from failing of views at the respective X-ray tube voltages.

In the case of the 180°+ fan angle half scan H-Scan in a manner similar to the above, the scan is carried out twice as shown in FIG. 2(*b*) to enable X-ray data acquisition corresponding to 180°+ fan angle, of low energy projection data RE1 and high energy projection data RE2.

Figure 5:
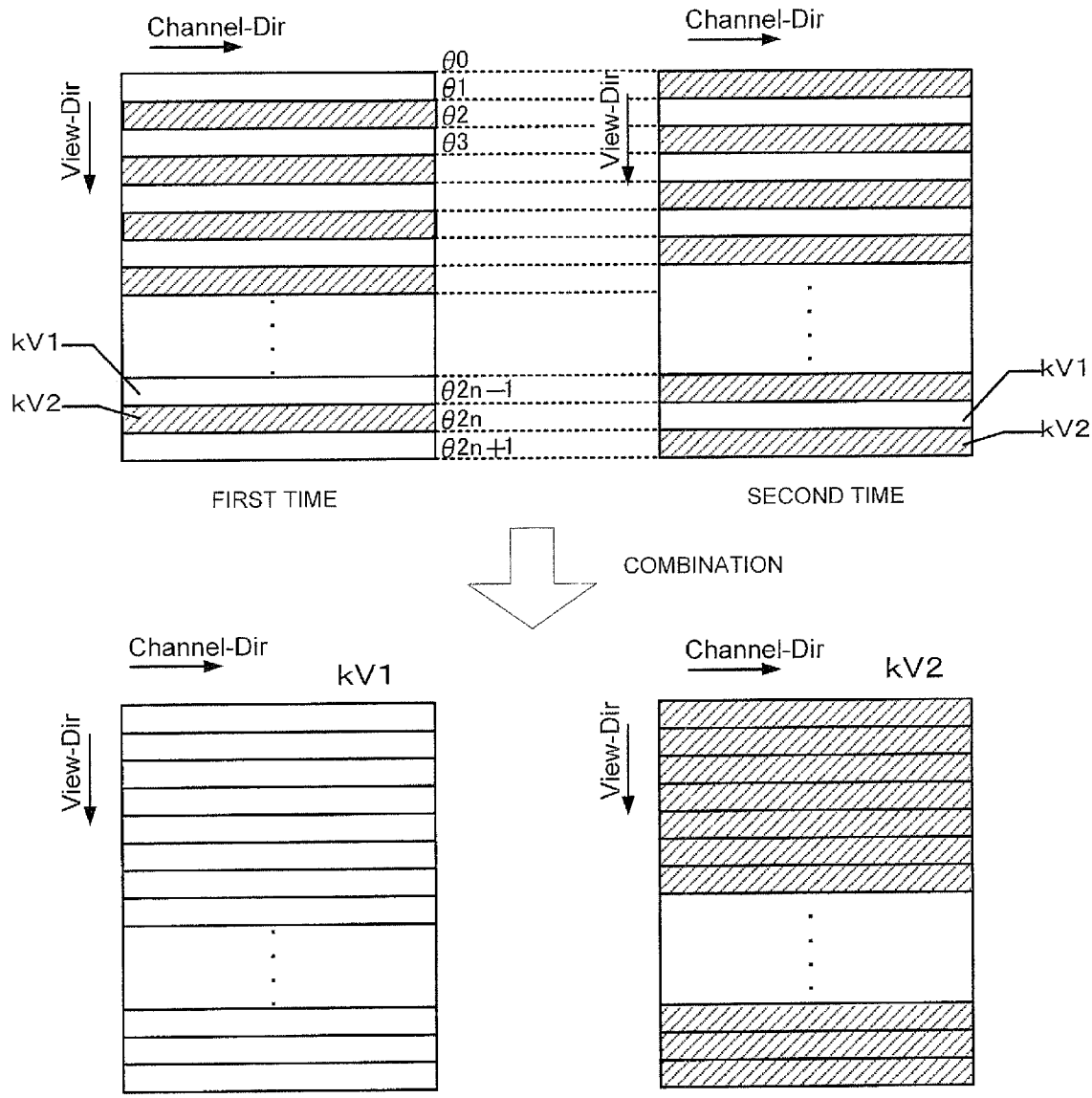
FIG. 5 is a diagram illustrating a combination of low energy projection data RE1 and high energy projection data RE2.

The low energy projection data RE1 and the high energy projection data RE2 are combined as shown in FIG. 5 to enable data acquisition with division into the low energy projection data RE1 and the high energy projection data RE2. Incidentally, when view-absent views exist as a result of their combination, view data can be obtained by performing interpolation processing on X-ray projection data corresponding to the adjacent views.

Assume that, for example, X-ray projection data D (k, row, ch), . . . D (k+n, row, ch) corresponding to a k view and a k+n view exist and X-ray projection data D (k+1, row, ch), . . . D (k+n−1, row, ch) from a k+1 view to a k+n−1 view do not exist. However, row and ch respectively represent a row of the multi-row X-ray detector 24 and the number of each channel. Also assume that $1 \leq i \leq n-1$. The X-ray projection data from the k+1 view to the k+n−1 view in this case are expressed as shown below in Equation (1) when interpolation or weighted addition is conducted using a linear interpolating process.

$$D(k+i, \text{row}, ch) = \frac{n-i}{n} \cdot D(k, \text{row}, ch) + \frac{i}{n} \cdot D(k+n, \text{row}, ch) \quad \text{Eq. (1)}$$

Although it is ideal that the switching between the X-ray tube voltages every view or several views is performed without switching time, the time is actually required for switching. This switching time becomes innegligible as the scan time taken for one rotation becomes fast, and the proportion of a transient voltage applied during the switching time also increases. Incidentally, the switching time depends even on the performance of a high-voltage generating device and the X-ray controller 22.

Figure 3:
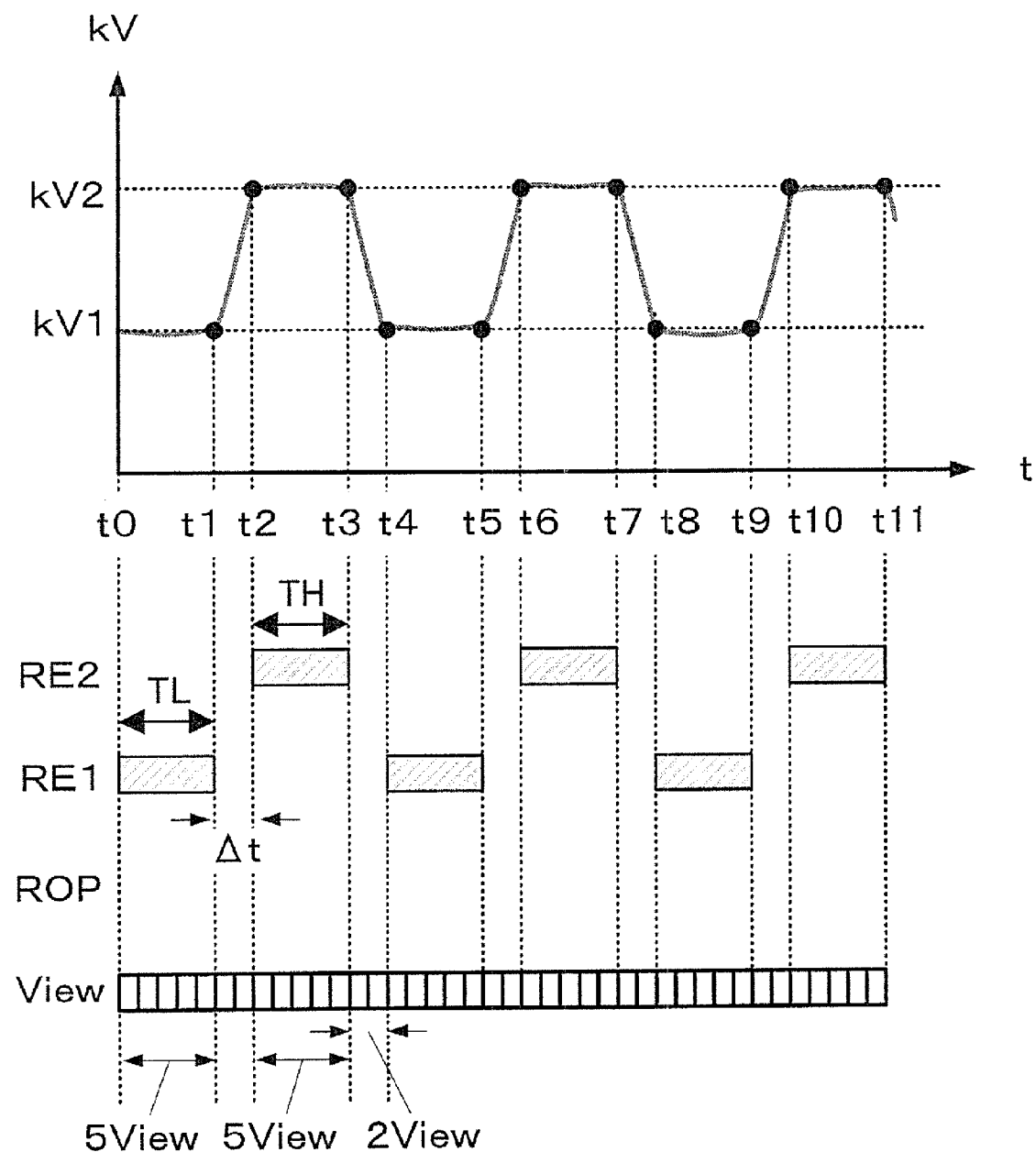
FIG. 3 is a diagram showing data acquisition timings at dual energy scanning.

For example, such X-ray data acquisition as shown in FIG. 3 illustrates where during one cycle or period, low energy projection data RE1 is acquired by five views, transient energy projection data REt is acquired by two views, high energy projection data RE2 is acquired by five views, and the transient energy projection data REt is acquired by two views again.

In this case, the efficiency of utilization of X-ray projection data reaches about 10/14=about 70% when no transient energy projection data REt is used. The efficiency e of X-ray utilization in a clockwise direction of FIG. 3 is generally expressed as follows:

$$e = \frac{TL + TH}{TL + TH + 2 \cdot \Delta t} \quad \text{Eq. (2)}$$

Therefore, it is considered that the transient energy projection data REt is also used in image reconstruction in order to consider exposure of a subject or subject to radiation and set the X-ray utilization efficiency e to 100% in the present embodiment.

A description will be made below of an example in which the transient X-ray projection data is used in the image reconstruction using the embodiment while the operation of the X-ray CT apparatus according to the present embodiment is being described.

Figure 4:
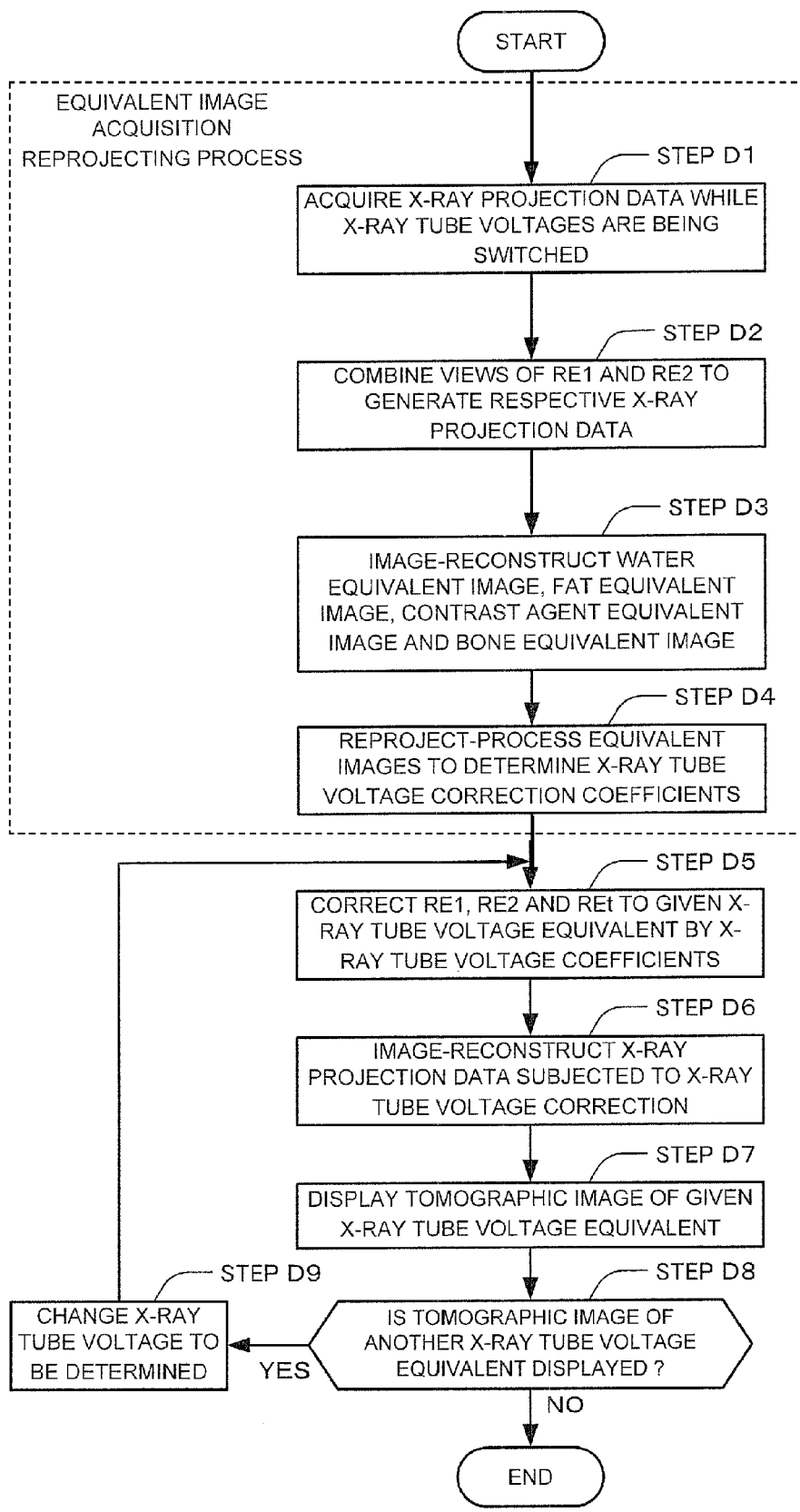
FIG. 4 is a flowchart for describing an X-ray tube voltage interpolating process for transient energy projection data REt.

FIG. 4 is a flowchart for correcting transient energy projection data REt through a twice-scan method for dual energy scanning.

At Step D1, the multi-row X-ray detector 24 switches between an X-ray by a low X-ray tube voltage kV1 and an X-ray by a high X-ray tube voltage kV2 to perform X-ray data acquisition. During the X-ray data acquisition, X-ray tube voltage information are obtained every view by X-ray tube voltage reference channels set to the X-ray controller 22, the multi-row X-ray detector 24 and the like. Incidentally, X-ray tube voltage information based on actual measurements or pre-measurements are obtained with respect to views corresponding to transient sections of X-ray tube voltages. X-ray projection data at the low X-ray tube voltage kV1 is set as low energy projection data RE1, and X-ray projection data at the high X-ray tube voltage kV2 is set as high energy projection data RE2.

At Step D2, the image reconstruction unit 34 uses views corresponding to the low energy projection data RE1 and the high energy projection data RE2 in parts respectively and thereby combines X-ray projection data. The image reconstruction unit 34 replenishes insufficient views by interpolation processing, based on X-ray projection data corresponding to adjacent views as needed. Incidentally, transient energy projection data REt is not contained here.

At Step D3, dual energy image reconstruction is performed to image-reconstruct a water equivalent image, a fat equivalent image, a contrast agent equivalent image and a bone equivalent image.

Figure 6:
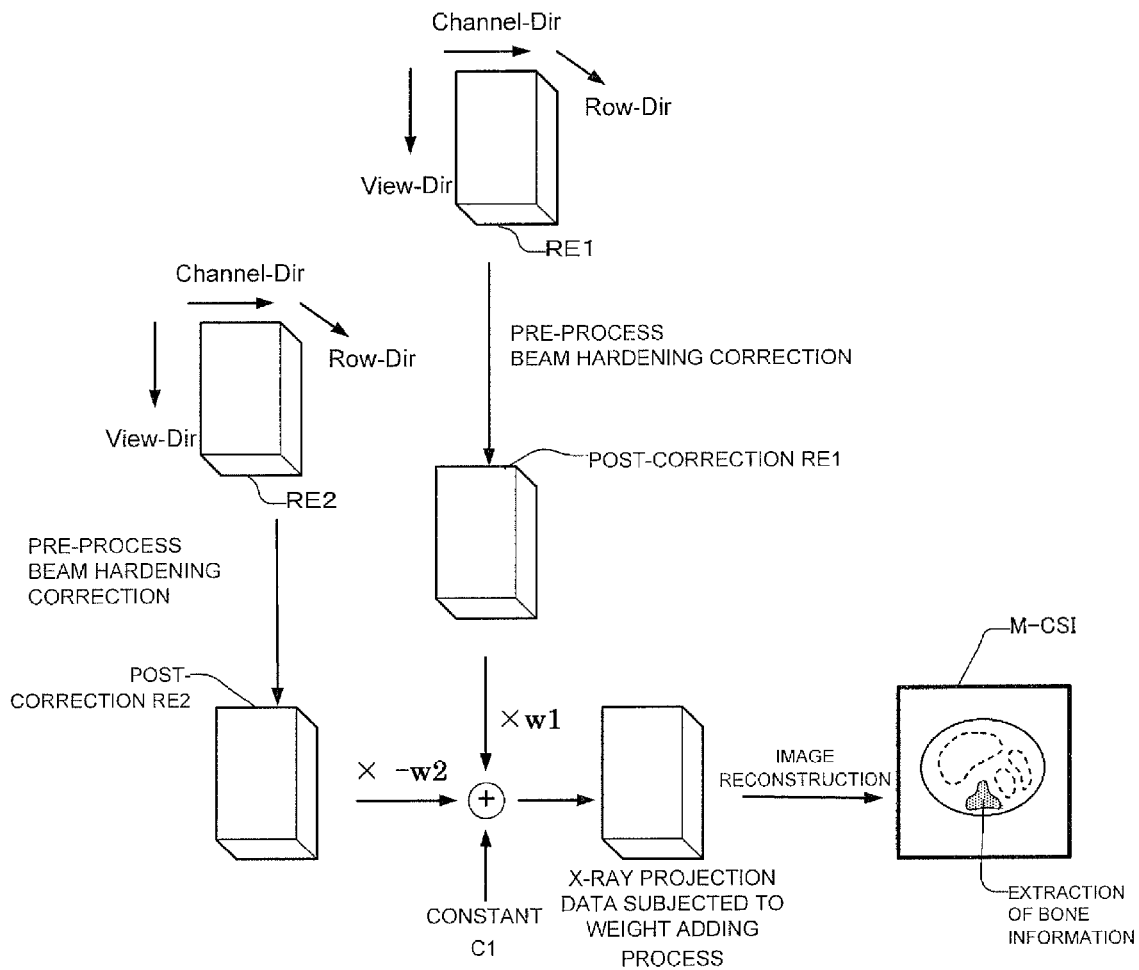
FIG. 6 is an image diagram for determining a tomographic image based on X-ray absorption coefficients in a projection data space.

The dual energy image reconstruction for obtaining the various types of equivalent images is as follows:

FIG. 6 shows the outline of a dual energy image reconstructing method in a projection data space.

First, low energy projection data RE1 is multiplied by a weighted addition coefficient w1 and high energy projection data RE2 is multiplied by a weighted addition coefficient w2 in like manner. Then, a weight adding process is performed together with a constant C1 to generate a dual energy tomographic image M-CSI.

These weighted addition coefficients w1 and w2 and constant C1 are determined depending on each atom desired to be extracted, each atom desired to be emphasized and each atom or region desired to be deleted on the display. When, for example, a calcium component (Ca component) that constitutes a bone and a calcified portion close to each other in CT value is deleted on the display, i.e., a pixel value is set to 0 in order to separate the calcium component and a contrast agent (Iodine component) with iodine as a principal component from each other at a weighted addition processing unit, a contrast agent component is extracted and can be displayed emphatically. On the other hand, when the contrast agent component is deleted on the display, i.e., the pixel value is set to 0 at the weighted addition processing unit, the calcium component is extracted and thereby the bone and calcified portion can be displayed emphatically.

As X-ray projection data used at this time, the X-ray projection data subjected to the pre-process and the beam hardening correction by the pre-processor 33 is used. By setting a substance unequivalent to water to an X-ray penetration path length equivalent to water at each X-ray tube voltage, the dependence of each substance other than water on each X-ray tube voltage can be evaluated more correctly in the beam hardening correction in particular.

Assuming that the pre-process and beam hardening correction have already been corrected by the pre-processor 34 even in a tomographic image space, the dual energy image reconstruction unit 35 is capable of image-reconstructing a dual energy tomographic image.

Referring back to FIG. 4, at Step D4, the image reconstruction unit 34 performs a reprojection process RP on the water equivalent image, fat equivalent image, contrast agent equivalent image and bone equivalent image thereby to obtain reprojection data of respective penetrated images. Substance information about the X-ray projection data acquired at Step D1 are obtained according to the reprojection data.

On the other hand, X-ray tube voltage correction coefficients can be determined based on X-ray absorption coefficients of respective substances at respective X-ray energy, i.e., the differences between X-ray absorption coefficients at respective X-ray tube voltages every substance. Thus, at Step D4, X-ray tube voltage correction coefficients for the X-ray projection data acquired at Step D1 are determined with respect to the X-ray projection data, based on the X-ray tube voltage information and corrected X-ray tube voltages set every view. Incidentally, there are known, as reprojection processes RP, a method for making image rotation in a θ direction to perform a reprojection process RP, and a method for performing shift processing to perform a reprojection process RP.

FIG. 7 is a conceptual diagram showing a method for performing image rotation in a θ direction to perform a reprojection process RP.

In the reprojection process, a pixel value of an (x, y) coordinate of a tomographic image is defined as g (x, y) and rotated in a θ direction to obtain a tomographic image (X, Y). Affine transformation corresponding to this coordinate transformation is represented as follows in Equation (3).

$$\begin{bmatrix} X \\ Y \end{bmatrix} = \begin{bmatrix} \cos\theta & -\sin\theta \\ \sin\theta & \cos\theta \end{bmatrix} \begin{bmatrix} x \\ y \end{bmatrix} \qquad \text{Eq. (3)}$$

Reprojection profile data Pθ (x) in the θ direction can be determined as follows in Equation (4). However, a matrix number for the tomographic image is defined as N×N pixels.

$$P\theta(x) = \sum_{Y=1}^{N} g(X, Y) \qquad \text{Eq. (4)}$$

Incidentally, profile data Pθ (x) can also be generated in like manner by performing a reprojection process RP on g (x, y) of the original tomographic image in the θ direction even without generating the tomographic image g (X, Y) rotated in the θ direction. Although a memory access time is taken for this processing, a simple algorithm may be performed by non-execution of needless processing.

Figure 8:
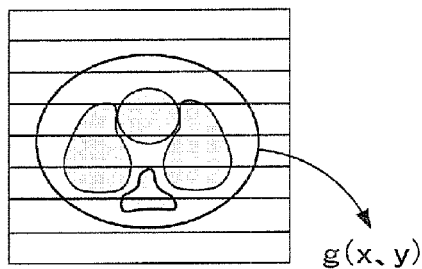
FIG. 8 is a diagram illustrating a method for shift-processing a tomographic image to perform reprojection process RP.
Figure 8:
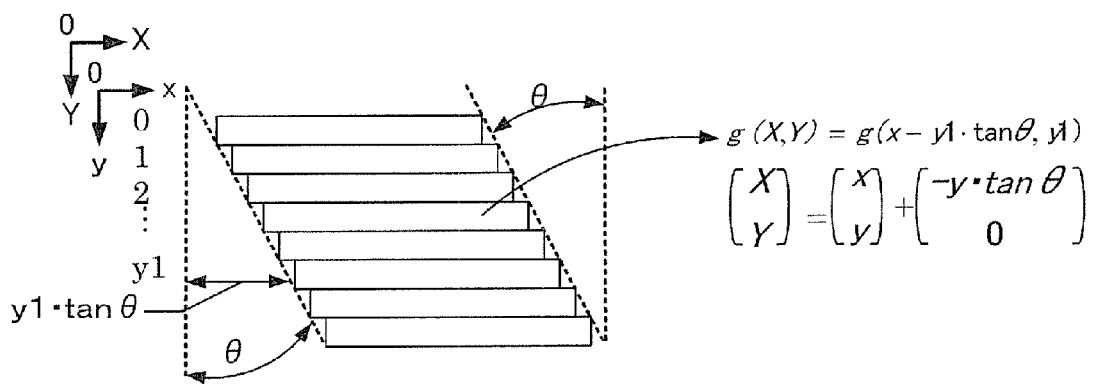
Figure 8:
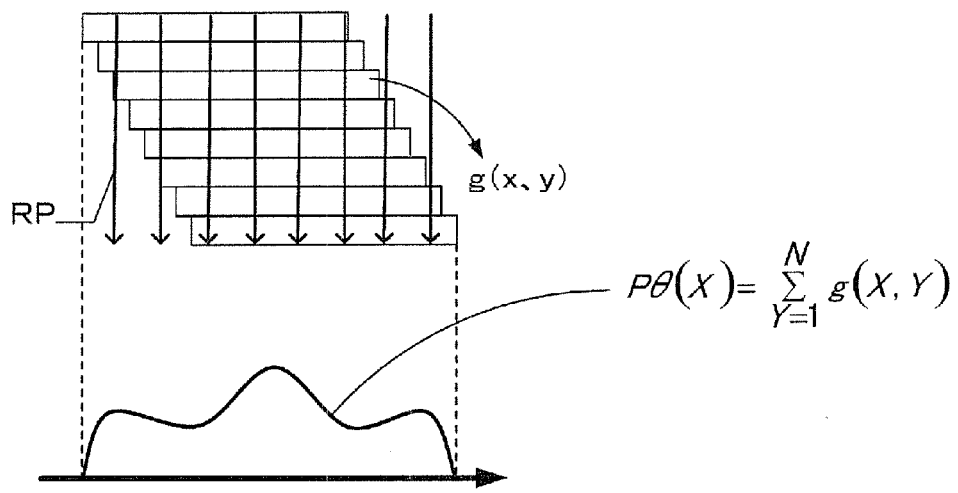

FIG. 8 is a conceptual diagram showing a method for performing a reprojection process RP by a shift process. In the shift process, a reprojection process RP using a parallel beam in an arbitrary θ direction can be performed. This process has the advantage in that the processing time is short as compared with the rotary system.

This reprojection process performs a shift process on one line data in an x direction at each y coordinate position of a tomographic image g (x, y).

As shown in FIG. 8, the reprojection process performs a shift process on one line data in the x direction at a y coordinate position of y=y1 with one line data being shifted in the x direction by −y1·tan θ and performs it on all y coordinate values.

The equations for coordinate transformation at this time are expressed as follows in Equation (5) and Equation (6).

However, assume that (X, Y) indicates a coordinate subsequent to the coordinate transformation, and (x, y) indicates a coordinate prior to the coordinate transformation.

$$\begin{bmatrix} X \\ Y \end{bmatrix} = \begin{bmatrix} x \\ y \end{bmatrix} + \begin{bmatrix} -y \cdot \tan\theta \\ 0 \end{bmatrix} \qquad \text{Eq. (5)}$$

$$g(X, Y) = g(x - y, \tan\theta \cdot y) \qquad \text{Eq. (6)}$$

Referring back to FIG. 4, at Step D5, the conversion processor 35 corrects each of views for X-ray tube voltages to a predetermined X-ray tube voltage equivalent kVa. In the present embodiment, the low energy projection data RE1, high energy projection data RE2 and transient energy projection data REt are also corrected to be X-ray projection data corresponding to the predetermined X-ray tube voltage equivalent kVa.

At Step D6, the image reconstruction unit 34 image-reconstructs the X-ray projection data subjected to the X-ray tube voltage correction.

At Step D7, an image display unit displays a tomographic image having the predetermined X-ray tube voltage equivalent kVa.

At Step D8, an operator determines whether a tomographic image having another X-ray tube voltage equivalent kVa should be displayed. If the answer is found to be YES, then the operator proceeds to Step D9. If the answer is found to be NO, then the operator terminates the processing.

At Step D9, the X-ray tube voltage to be determined is changed.

A method for verifying whether an X-ray tube voltage correction is performed properly, will next be explained in the present embodiment. Incidentally, there is a possibility that when an X-ray voltage correction at a transient section has not been performed properly, discontinuity of X-ray projection data will occur and artifacts will occur in a tomographic image.

Figure 9:
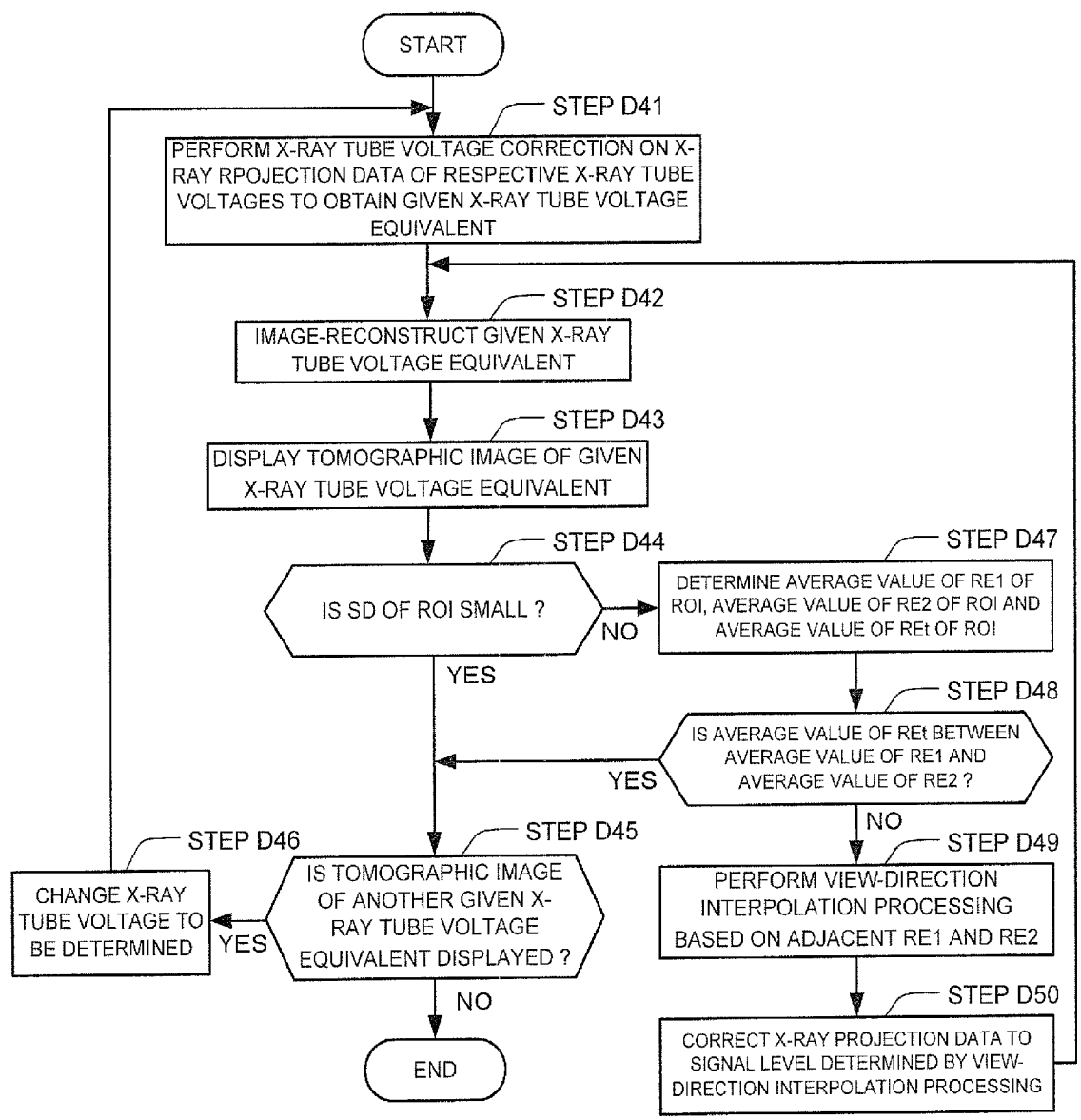
FIG. 9 is a flowchart for describing an artifact reducing process.

FIG. 9 is a flowchart showing one example illustrative of a process for verifying whether an X-ray tube voltage correction is performed properly and an artifact reducing process where it is performed improperly.

At Step D41, the conversion processor 35 performs an X-ray tube voltage correction on X-ray projection data of each X-ray tube voltage to reach or obtain a predetermined X-ray tube voltage equivalent kVa.

At Step D42, the image reconstruction unit 34 image-reconstructs the predetermined X-ray tube voltage equivalent kVa.

At Step D43, the image display unit displays a tomographic image corresponding to the predetermined X-ray tube voltage equivalent kVa.

At Step D44, it is determined whether a standard deviation value SD of a region of interest ROI of each air portion is small. If the answer is found to be YES, the processing proceeds to Step D45. If the answer is found to be NO, then the processing proceeds to Step D47.

Figure 10:
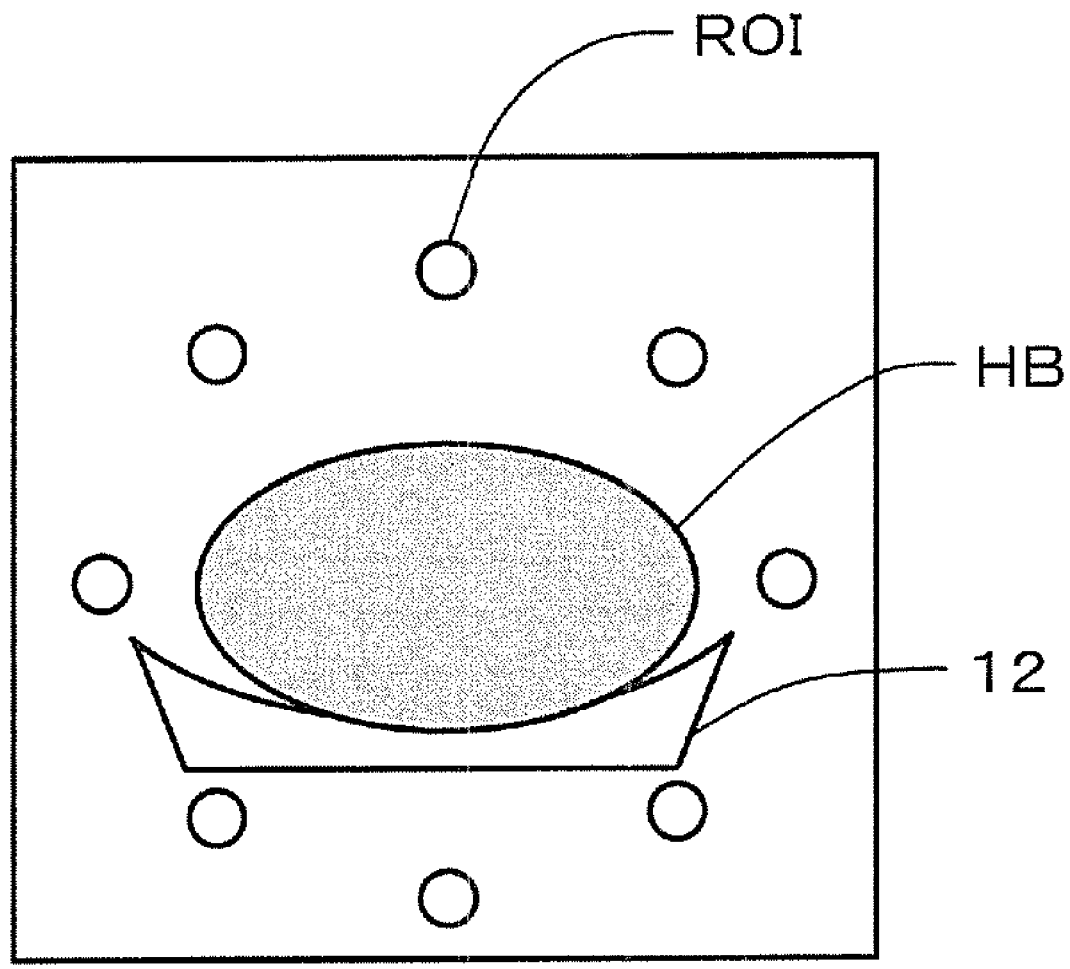
FIG. 10 is a diagram showing regions of interest ROI of air portions.

FIG. 10 shows one example illustrative of regions of interest ROI of air portions by way of example. Regions of interest ROI of eight air portions are set to a peripheral portion in avoidance of the subject and the cradle 12 of the photographing table 10 as their set positions. The regions of interest ROI are not necessarily limited to eight, but may be four regions or one region. If the regions of interest ROI are not brought into contact with the subject and the cradle 12, then they may not be set to a peripheral region. When the value of each region of interest ROI indicates a value higher than the air's standard deviation value SD determined from its imaging condition, an X-ray tube voltage correcting unit 38 can predict that artifacts will occur.

At Step D45, the operator determines whether a tomographic image of another predetermined X-ray tube voltage equivalent kVa is displayed. If the answer is found to be YES, then the operator proceeds to Step D46. If the answer is found to be NO, then the operator terminates the processing.

At Step D46, the X-ray tube voltage correcting unit 38 changes an X-ray tube voltage to be determined. Thereafter it returns to Step D41.

At Step D47, the X-ray tube voltage correcting unit 38 determines the average value of low energy projection data RE1, the average value of high energy projection data RE2 and the average value of transient energy projection data REt for the air portions or regions.

At Step D48, it is determined whether the average value of the transient energy projection data REt exists between the average value of the low energy projection data RE1 and the average value of the high energy projection data RE2. If the answer is found to be YES, then the processing proceeds to Step D45. If the answer is found to be NO, then the processing proceeds to Step D49.

At Step D49, the X-ray tube voltage correcting unit 38 performs view-direction interpolation processing, based on low energy projection data RE1 of an X-ray tube voltage 80 kV and high energy projection data RE2 of an X-ray tube voltage 140 kV both of which are adjacent to each other.

Thus, the image reconstruction unit 34 can obtain a tomographic image good in S/N without needless exposure because all views including the transient energy projection data REt are used.

Incidentally, although the low energy projection data RE1, in Step D50 the high energy projection data RE2 and the transient energy projection data REt are also corrected to be the X-ray projection data corresponding to the predetermined X-ray tube voltage equivalent kVa in the present embodiment, only the transient energy projection data REt may be corrected to the X-ray tube voltage equivalent for obtaining an X-ray tube voltage equivalent or high energy for obtaining low energy, for example.

In a second embodiment, low energy projection data RE1 and high energy projection data RE2 corresponding to main X-ray projection data are subjected to an X-ray tube voltage correction so as to reach a predetermined X-ray tube voltage equivalent kVa. Transient energy projection data REt makes use of X-ray projection data determined by performing interpolation processing in a view direction. A noise reducing process based on a noise component of the transient energy projection data REt is performed on the X-ray projection data subjected to the interpolation processing in the view direction. It is thus possible to obtain a tomographic image good in S/N without needless exposure using all views for the X-ray projection data.

Figure 11:
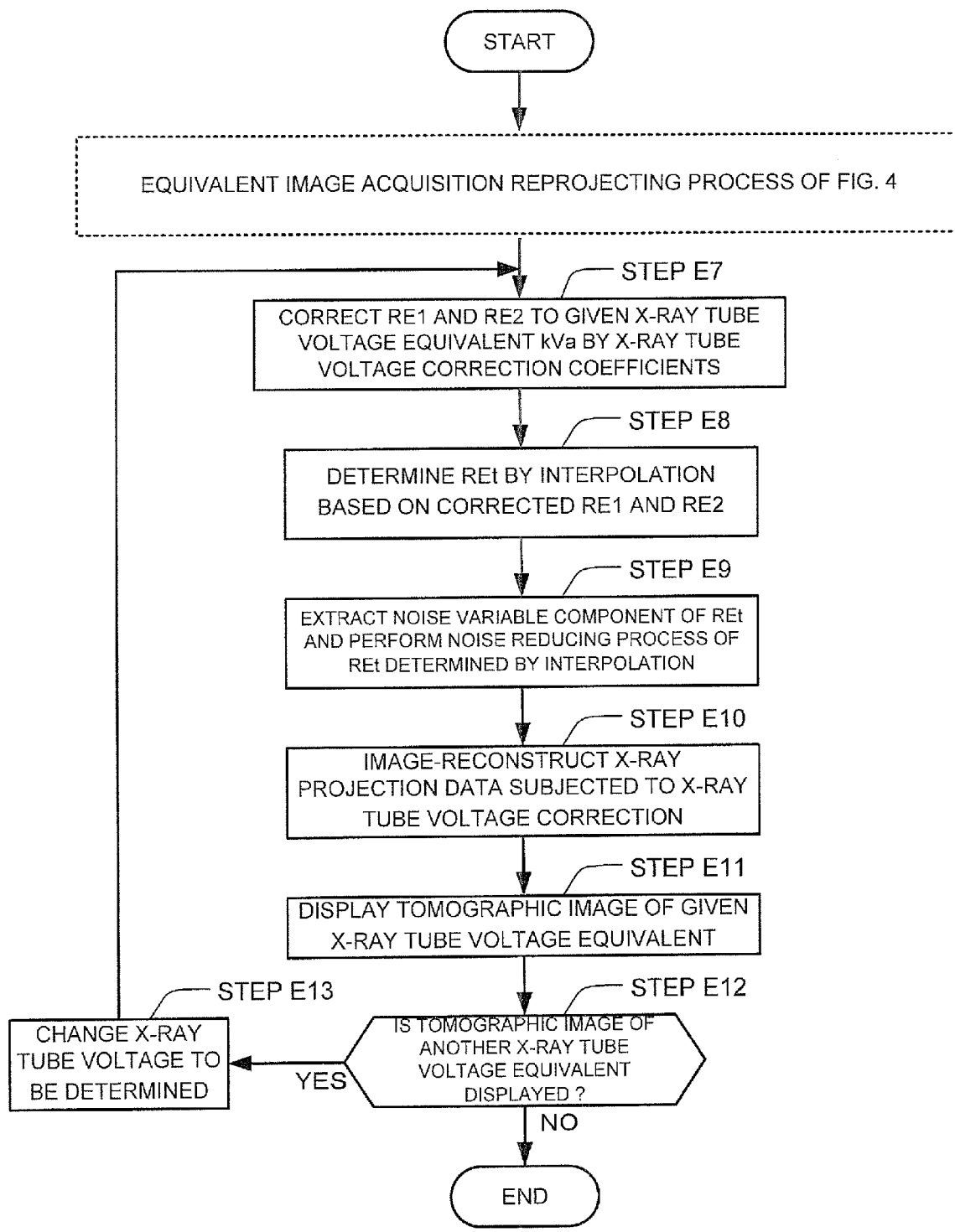
FIG. 11 is a flowchart for describing a noise reducing process based on transient energy projection data REt.

FIG. 11 shows a flowchart for describing the processing included in the second embodiment.

Processes up to Step E7 are similar to the equivalent-image reprojection process RP from Step D1 to Step D4 shown in FIG. 4.

At Step E7, the image reconstruction unit 34 corrects the low energy projection data RE1 and the high energy projection data RE2 to the predetermined X-ray tube voltage equivalent kVa by the X-ray tube voltage correction coefficients determined at Step D4. At this time, the X-ray tube voltage correction for the transient energy projection data REt is not performed.

At Step E8, the image reconstruction unit 34 interpolates the transient energy projection data REt by interpolation processing or a weight adding process, based on the low energy projection data RE1 and the high energy projection data RE2.

At Step E9, the conversion processor 35 extracts a noise variable component of the transient energy projection data REt and adds it to the X-ray projection data determined based on the low energy projection data RE1 and the high energy projection data RE2 in the direction to cancel out noise thereby to perform the process of conversion of the transient energy projection data.

Figure 12:
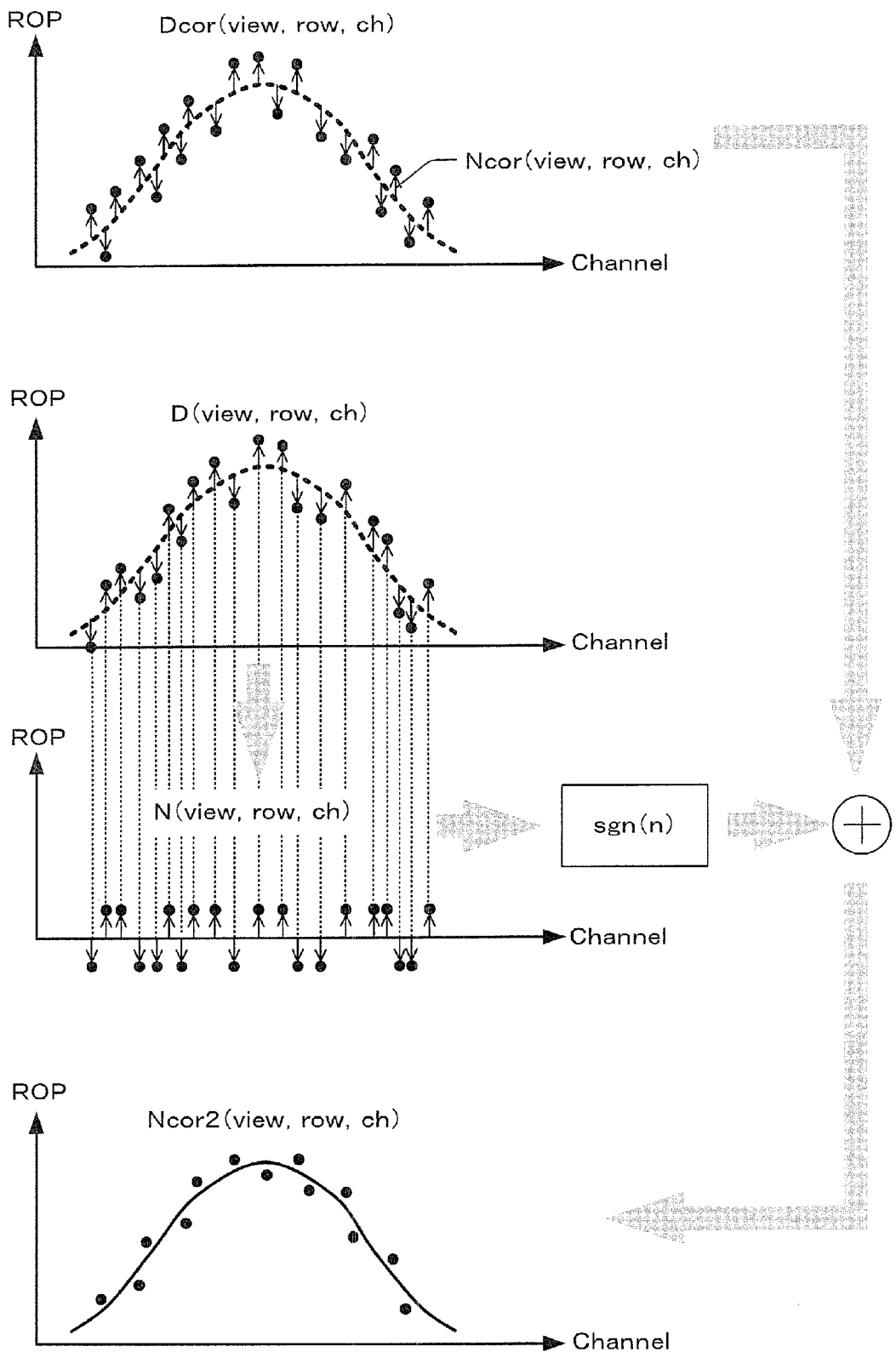
FIG. 12 is a diagram showing the outline of the noise reducing process for X-ray projection data.

FIG. 12 shows the outline of the noise reducing process.

Assuming that X-ray projection data subjected to interpolation processing and a weight adding process, based on low energy projection data RE1 and high energy projection data RE2 is Dcor (view, row, ch), a noise variable component Ncor (view, row, ch) can be determined using Equation (7).

$$N\text{cor}(\text{view,row,ch})=D\text{cor}(\text{view,row,ch})-D\text{cor}(\text{view,row,ch})*\text{Low Pass Filter}(\text{row,ch})\quad\text{Eq. (7)}$$

where the Low Pass Filter (row, ch) is assumed to be a low pass filter in a channel direction or low pass filters in row and channel directions. The "*" operator indicates convolution.

Assuming that transient energy projection data REt is D (view, row, ch) and its noise variable component is N (view, row, ch), the noise variable component can be determined by Equation (8).

$$N(\text{view,row,ch})=D(\text{view,row,ch})-D(\text{view,row,ch})*\text{Low Pass Filter}(\text{row,ch})\quad\text{Eq. (8)}$$

Incidentally, the Low Pass Filter (row, ch) at this time may be one identical to that used in Equation (9).

Assuming now that a function for determining positive and negative signs of a given numeric value is sgn (n), for example, sgn (n)=1 at n≧0, and sgn (n)=−1 at n<0.

Assuming that at this time, the noise variable component is N (view, row, ch) and the result of a noise reducing process is Ncor2 (view, row, ch), such a relational expression as given by Equation (9) is established.

$$N\text{cor2}(\text{view,row,ch})=N\text{cor}(\text{view,row,ch})-\text{sgn}(N\text{cor}(\text{view,row,ch}))\cdot N(\text{view,row,ch})\quad\text{Eq. (9)}$$

At Step E10, the image reconstruction unit 34 performs image reconstruction using the low energy projection data RE1 and high energy projection data RE2 subjected to the X-ray tube voltage correction, and the X-ray projection data determined by the low energy projection data RE1 and high energy projection data RE2 subsequent to execution of the noise reducing process using the noise component extracted from the transient energy projection data at the conversion processor 35.

At Step E11, the image display unit displays a tomographic image corresponding to a predetermined X-ray tube voltage equivalent kVa.

At Step R12, the operator determines whether a tomographic image corresponding to another X-ray tube voltage equivalent kVa is displayed. If the answer is found to be YES, then the operator proceeds to Step E13. If the answer is found to be NO, then the operator terminates the processing.

At Step E13, the operator changes an X-ray tube voltage to be determined.

Incidentally, the cine display of the tomographic image of the X-ray tube voltage equivalent kVa obtained in each of the first and second embodiments can make it easy for the operator to visually grasp composition information of a subject.

In order to perform the cine display, the X-ray tube voltage correcting unit 38 sets within the range of the X-ray tube voltage according to the imaging or scanning condition setting in advance and generates all of tomographic images of X-ray tube voltage equivalents kVa lying therewithin. The image display unit continuously displays the dependence of respective portions or regions on the X-ray tube voltages by using the generated tomographic images and performing the cine display processing. It is thus possible to make it easy for the operator to recognize the difference in composition visually.

Although each of the first and second embodiments has described the image reconstruction for the dual energy scanning at the image space processing centrally, a similar advantage can be brought about even in the case of image reconstruction for the dual energy scanning in a projection data space. Although 80 kV is used for the low energy projection data RE1 and 140 kV is used for the high energy projection data RE2 in the first and second embodiments, similar dual energy scanning can be performed even at other X-ray tube voltages, and a similar advantage can be brought about.

Although the present embodiment has described the case in which the X-ray automatic exposure mechanism of the X-ray CT apparatus 100 is not used, a similar advantage can be brought about even where the X-ray automatic exposure mechanism of the X-ray CT apparatus 100 is used.

Although the present embodiment has described the case in which the X-ray data acquisition is not synchronized with a biological signal, a similar advantage can be brought about even though the X-ray data acquisition is synchronized with the biological signal, particularly, a cardiac signal. Although the present embodiment has described the X-ray CT apparatus 100 having the two-dimensional X-ray area detector of the matrix structure, which is typified by the multi-row X-ray detector or the flat panel X-ray detector, a similar advantage can be brought about even in the case of an X-ray CT apparatus 100 having a one-row X-ray detector. Further, although the present embodiment has been described on the basis of the X-ray CT apparatus 100, it can be applied even to an X-ray CT-PET apparatus, an X-ray CT-SPEC apparatus and the like combined with other apparatus.

What is claimed is:

1. An X-ray CT apparatus comprising:
    an X-ray irradiation unit configured to apply X-rays based on a first X-ray tube voltage and X-rays based on a second X-ray tube voltage different from the first X-ray tube voltage to a subject by being switched every at least one view;
    a projection data acquisition unit configured to acquire projection data of the X-rays applied to the subject, the projection data identifying X-ray tube voltage information about the applied X-rays; and
    an image reconstruction unit configured to identify first energy projection data of the X-rays based on the first X-ray tube voltage, second energy projection data of the X-rays based on the second X-ray tube voltage, and transient energy projection data acquired upon switching between the first X-ray tube voltage and the second X-ray tube voltage based on the X-ray tube voltage information, said image reconstruction unit comprising a conversion processor configured to convert at least the transient energy projection data to another data using the transient energy projection data, and to perform image reconstruction using at least the data subsequent to the conversion process.

2. The X-ray CT apparatus according to claim 1, wherein said conversion processor is configured to perform an X-ray tube voltage correcting process using X-ray tube voltage correction coefficients for correcting the transient energy projection data to projection data equivalent to a predetermined X-ray tube voltage.

3. The X-ray CT apparatus according to claim 2, wherein said conversion processor is configured to use the X-ray tube voltage correcting process to identify a substance of the subject with respect to the transient energy projection data and to use an X-ray tube voltage correction coefficient corresponding to the substance.

4. The X-ray CT apparatus according to claim 3, wherein the X-ray tube voltage correcting process performed by said conversion processor includes a process for correcting the first energy projection data, the second energy projection data and the transient energy projection data to projection data equivalent to the same X-ray tube voltage.

5. The X-ray CT apparatus according to claim 4, wherein the X-ray tube voltage correcting process performed by said conversion processor includes a process for verifying whether the correction of the transient energy projection data is proper.

6. The X-ray CT apparatus according to claim 3, wherein the image reconstruction unit is configured to image-reconstruct a tomographic image equivalent to a desired X-ray tube, voltage based on the post-correction first energy projection data, the second energy projection data, and the transient energy projection data.

7. The X-ray CT apparatus according to claim 2, wherein said conversion processor is configured to identify the substance of the subject with respect to the transient energy projection data based on projection data obtained by performing a reprojection process one of a dual energy tomographic image based on weighted addition of the first energy projection data and the second energy projection data and a dual energy tomographic image obtained by weighted adding a first tomographic image based on the first X-ray projection data and a second tomographic image based on the second X-ray projection data.

8. The X-ray CT apparatus according to claim 7, wherein the dual energy tomographic image includes at least one of a water equivalent image, a fat equivalent image, a bone equivalent image or a contrast agent equivalent image.

9. The X-ray CT apparatus according to claim 1, wherein said conversion processor is configured to calculate X-ray projection data substituted for the transient energy projection data by interpolation processing based on the first energy projection data and the second energy projection data, to extract a noise variable component from the transient energy projection data, and to perform a noise reducing process using the noise variable component on the X-ray projection data substituted for the transient energy projection data.

10. The X-ray CT apparatus according to claim 9, wherein said conversion processor is configured to perform a process for correcting the first energy projection data and the second energy projection data to projection data equivalent to the same X-ray tube voltage.

11. The X-ray CT apparatus according to claim 10, wherein said conversion processor is configured to perform interpolation processing based on the first energy projection data and the second energy projection data using the post-correction first energy projection data and second energy projection data.

12. The X-ray CT apparatus according to claim 10, wherein said image reconstruction unit is configured to image-reconstruct a tomographic image equivalent to a desired X-ray tube voltage based on the post-correction first energy projection data, the second energy projection data, and the data subjected to the noise reducing process.

13. The X-ray CT apparatus according to claim 1, wherein said X-ray irradiation unit is configured to perform one of a 360° full scan by two scans and a 180°+ fan angle half scan by two scans.

14. The X-ray CT apparatus according to claim 13, wherein said X-ray irradiation unit is configured to interchange the first X-ray tube voltage and the second X-ray tube voltage at a first scan and a second scan.

15. The X-ray CT apparatus according to claim 1, wherein said image reconstruction unit is configured to calculate one of first energy projection data and second energy projection data in a view direction insufficient to acquire X-ray projection data based on one of a first X-ray tube voltage by a 360° full scan and a 180°+ fan angle by interpolation processing.

16. A method for processing X-ray projection data, comprising steps of:
    identifying first energy projection data of X-rays based on a first X-ray tube voltage, second energy projection data of X-rays based on a second X-ray tube voltage different from the first X-ray tube voltage, and transient energy projection data acquired upon switching between the first X-ray tube voltage and the second X-ray tube voltage, based on X-ray tube voltage information identified for projection data obtained by X-ray CT apparatus, wherein the projection data is acquired by irradiating X-rays based on the first X-ray tube voltage and X-rays based on the second X-ray tube voltage to a subject by being switched every at least one view;

conversion processing at least the transient energy projection data to another data using the transient energy projection data; and performing image reconstruction using at least the data subsequent to the conversion process.

17. A method for processing X-ray projection data according to claim 16, wherein conversion processing comprises performing an X-ray tube voltage correcting process using X-ray tube voltage correction coefficients for correcting the transient energy projection data to projection data equivalent to a predetermined X-ray tube voltage.

18. A method for processing X-ray projection data according to claim 17, wherein conversion processing comprises correcting the first energy projection data, the second energy projection data and the transient energy projection data to projection data equivalent to the same X-ray tube voltage.

19. A method for processing X-ray projection data according to claim 17, wherein performing an X-ray tube voltage correcting process comprises identifying a substance of the subject with respect to the transient energy projection data and using an X-ray tube voltage correction coefficient corresponding to the substance.

20. A method for processing X-ray projection data according to claim 16, wherein conversion processing comprises calculating X-ray projection data substituted for the transient energy projection data by interpolation processing based on the first energy projection data and the second energy projection data, extracting a noise variable component from the transient energy projection data, and performing a noise reducing process using the noise variable component on the X-ray projection data substituted for the transient energy projection data.

* * * * *